(12) United States Patent
Ruezinsky et al.

(10) Patent No.: US 8,692,068 B2
(45) Date of Patent: Apr. 8, 2014

(54) PROMOTER MOLECULES FOR USE IN PLANTS

(75) Inventors: Diane M. Ruezinsky, Grover, MO (US); Crystal L. Hewitt, Canton, MA (US); Wei Zheng, Davis, CA (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 13/174,745

(22) Filed: Jun. 30, 2011

(65) Prior Publication Data

US 2012/0022235 A1    Jan. 26, 2012

Related U.S. Application Data

(62) Division of application No. 11/939,493, filed on Nov. 13, 2007, now Pat. No. 7,999,094, which is a division of application No. 11/234,830, filed on Sep. 23, 2005, now Pat. No. 7,294,711.

(60) Provisional application No. 60/613,081, filed on Sep. 24, 2004.

(51) Int. Cl.
    *C12N 15/82* (2006.01)
    *C12N 15/87* (2006.01)
    *A01H 1/00* (2006.01)
    *C12N 15/00* (2006.01)

(52) U.S. Cl.
    USPC .................... 800/287; 800/278; 435/320.1

(58) Field of Classification Search
    USPC .......................................... 800/287
    See application file for complete search history.

(56) References Cited

U.S. PATENT DOCUMENTS

| | | | |
|---|---|---|---|
| 5,391,725 A | 2/1995 | Coruzzi et al. | 800/300 |
| 5,428,147 A | 6/1995 | Barker et al. | 536/24.1 |
| 5,447,858 A | 9/1995 | Key et al. | 435/6 |
| 5,589,583 A | 12/1996 | Klee et al. | 800/298 |
| 5,608,144 A | 3/1997 | Baden et al. | 800/287 |
| 5,614,399 A | 3/1997 | Quail et al. | 435/424 |
| 5,633,435 A | 5/1997 | Barry et al. | 800/300 |
| 5,633,441 A | 5/1997 | De Greef et al. | 800/271 |
| 5,898,096 A | 4/1999 | Klee et al. | 800/298 |
| 6,096,950 A | 8/2000 | John | 800/314 |
| 6,232,526 B1 | 5/2001 | McElroy et al. | 800/278 |
| 6,359,197 B1 | 3/2002 | Amasino et al. | 800/290 |
| 6,426,447 B1 | 7/2002 | Knauf et al. | |
| 6,448,387 B1 | 9/2002 | Slater et al. | 536/23.1 |
| 6,506,565 B1 | 1/2003 | Conner et al. | 435/6 |
| 6,914,171 B2 | 7/2005 | Charne et al. | 800/306 |
| 7,294,711 B2 | 11/2007 | Ruezinsky et al. | 800/278 |
| 7,417,177 B2 | 8/2008 | Ruezinsky et al. | 800/278 |
| 2002/0120962 A1* | 8/2002 | Charne et al. | 800/295 |
| 2006/0064776 A1 | 3/2006 | Ruezinsky et al. | 800/281 |
| 2006/0064777 A1 | 3/2006 | Ruezinsky et al. | 800/281 |
| 2009/0169709 A1 | 7/2009 | Ruezinsky et al. | 536/24.1 |

FOREIGN PATENT DOCUMENTS

| | | |
|---|---|---|
| WO | WO 00/74471 | 12/2000 |
| WO | WO 02/097103 | 12/2002 |

OTHER PUBLICATIONS

Kagaya et al., "The promoter from the rice nuclear gene encoding chloroplast aldolase confers mesophyll-specific and light-regulated expression in transgenic tobacco", *Mol. Gen. Genet* 248:668-674, 1995.
Pryde et al., "Compositions of Soybean Oil" Chapter 2, In: *Handbook of soy oil processing and utilization. USDS*, pp. 13-31, 1980.
Andreasson et al., "Age-dependent wound induction of a myrosinase-associated protein from oilseed rape (*Brassica napus*)," *Plant Molecular Biology*, 41:171-180, 1999.
Cho et al., "Regulation of root hair initiation and expansin gene expression in arabidopsis," *The Plant Cell*, 14:3237-3253, 2002.
Database EMBL, "B0HBX36TR B0HB *Brassica oleracea* genomic clone B0HBX36, DNA sequence," Database accession No. BH477556, 2001.
Database EMBL, "odf97d10.gl B.oleracea002 *Brassica oleracea* genomic, DNA sequence," Database accession No. BH933900, 2002.
GenBank Accession No. AR201519, 2002.
Kim et al., "A 20 nucleotide upstream element is essential for the nopaline synthase (nos) promoter activity," *Plant Molecular Biology*, 24:105-117, 1994.
Molhoj et al., "Expression of a membrane-anchored endo-1, 4-beta-glucanase from *Brassica napus*, orthologous to K0R from *Arabidopsis thaliana*, is inversely correlated to elongation in light-grown plants," *Plant Molecular Biology*, 45:93-105, 2001.
NCBI accession No. AF089848, "*Brassica napus* senescence-specific cysteine protease (SAG12-1) gene," complete cds, Nov. 30, 1999.
Noh et al, "Regulation of developmental senescence is conserved between *Arabidopsis* and *Brassica napus*," *Plant Molecular Biology*, 41:195-206, 1999.
Piechulla et al., "Identification of tomato Lhc promoter regions necessary for circadian expression," *Plant Molecular Biology*, 38:655-662, 1998.
Sander et al., "Analysis of a dehiscence zone endo-polygalacturonase in oilseed rape (*Brassica napus*) and *Arabidopsis thaliana*: Evidence for roles in cell separation in dehiscence and abscission zones, and in stylar tissues during pollen tube growth," *Plant Molecular Biology*, 46:469-479, 2001.
Welsch et al., "Structural and functional characterizatio of the phytoene synthase promoter from *Arabidopsis thaliana*," *Planta*, 216:523-534, 2003.

* cited by examiner

*Primary Examiner* — Li Zheng
(74) *Attorney, Agent, or Firm* — Dentons US LLP; Carine M. Doyle, Esq.

(57) ABSTRACT

The present invention relates to polynucleotide molecules for regulating gene expression in plants. In particular, the present invention relates to promoters isolated from *Brassica napus* that are useful for regulating gene expression of heterologous polynucleotide molecules in plants. The present invention also relates to expression constructs and transgenic plants containing the heterologous polynucleotide molecules.

20 Claims, No Drawings

PROMOTER MOLECULES FOR USE IN PLANTS

This application is a divisional of U.S. application Ser. No. 11/939,493 filed Nov. 13, 2007, now U.S. Pat. No. 7,999,094, which is a divisional of U.S. application Ser. No. 11/234,830, now U.S. Pat. No. 7,294,711, filed Sep. 23, 2005; which application claims the priority of provisional application Ser. No. 60/613,081, filed Sep. 24, 2004; each of the disclosures of which are incorporated herein by reference in their entireties.

BACKGROUND OF THE INVENTION

1. Field of the Invention

The present invention relates to the field of plant molecular biology and plant genetic engineering and more specifically relates to polynucleotide molecules useful for the expression of transgenes in plants.

2. Description of Related Art

One of the goals of plant genetic engineering is to produce plants with agronomically desirable characteristics or traits. Advances in genetic engineering have provided the requisite tools to transform plants to contain and express foreign genes. The technological advances in plant transformation and regeneration have enabled researchers to take an exogenous polynucleotide molecule, such as a gene from a heterologous or native source, and incorporate that polynucleotide molecule into a plant genome. The gene can then be expressed in a plant cell to exhibit the added characteristic or trait. In one approach, expression of a gene in a plant cell or a plant tissue that does not normally express such a gene may confer a desirable phenotypic effect. In another approach, transcription of a gene or part of a gene in an antisense orientation may produce a desirable effect by preventing or inhibiting expression of an endogenous gene.

For production of transgenic plants with various desired characteristics, it would be advantageous to have a variety of promoters to provide gene expression such that a gene is transcribed efficiently in the amount necessary to produce the desired effect. The commercial development of genetically improved germplasm has also advanced to the stage of introducing multiple traits into crop plants, often referred to as a gene stacking approach. In this approach, multiple genes conferring different characteristics of interest can be introduced into a plant. It is often desired when introducing multiple genes into a plant that each gene is modulated or controlled for optimal expression, leading to a requirement for diverse regulatory elements. In light of these and other considerations, it is apparent that optimal control of gene expression and regulatory element diversity are important in plant biotechnology.

Numerous promoters, which are active in plant cells, have been described in the literature. These include the nopaline synthase (nos) promoter and octopine synthase (ocs) promoters carried on tumor-inducing plasmids of *Agrobacterium tumefaciens* and the caulimovirus promoters such as the Cauliflower Mosaic Virus (CaMV) 19S or 35S promoter (U.S. Pat. No. 5,352,605), CaMV 35S promoter with a duplicated enhancer (U.S. Pat. Nos. 5,164,316; 5,196,525; 5,322,938; 5,359,142; and 5,424,200), and the Figwort Mosaic Virus (FMV) 35S promoter (U.S. Pat. No. 5,378,619). These promoters and numerous others have been used in the creation of constructs for transgene expression in plants. Other useful promoters are described, for example, in U.S. Pat. Nos. 5,391,725; 5,428,147; 5,447,858; 5,608,144; 5,614,399; 5,633,441; 6,232,526; and 5,633,435, all of which are incorporated herein by reference.

While previous work has provided a number of promoters useful to direct transcription in transgenic plants, there is still a need for novel promoters with beneficial expression characteristics. In particular, there is a need for promoters that are capable of directing expression of exogenous genes in dicotyledonous seeds. Many previously identified promoters fail to provide the patterns or levels of expression required to fully realize the benefits of expression of selected genes in transgenic plants. There is, therefore, a need in the art of plant genetic engineering for novel promoters for use in dicots.

SUMMARY OF THE INVENTION

The present invention relates to promoters that are described as silique wall preferred promoters. The phrase "silique wall preferred" refers to promoters that drive expression of operably linked genes to higher levels in the silique wall compared with any other tissue tested. Silique wall preferred promoters are useful for production of transgenic plants with desired seed traits. These include, but are not limited to, altering oil content, protein quality, cell proliferation, or micronutrient quality.

In one embodiment the present invention provides a promoter comprising a polynucleotide sequence substantially homologous to a polynucleotide sequence selected from the group consisting of SEQ ID NOs: 7, 8, and 9, or any fragments and variants thereof that are capable of regulating transcription of operably linked polynucleotide molecules, e.g., having promoter activity. In particular embodiments, a fragment of a sequence provided herein is defined as comprising at least about 30, 40, 50, 75, 100, 125, 150, 200, 250, 300, 350, 400, 450, 500, 600, 750, 900, 1000, or more contiguous nucleotides of any of the promoter sequences described herein, including, for example, SEQ ID NO: SEQ ID NOs: 7, 8, and 9.

In another embodiment, the present invention provides a plant expression construct comprising a promoter comprising a polynucleotide sequence substantially homologous to a polynucleotide sequence described herein, for example, selected from the group consisting of SEQ ID NOs: 7, 8, and 9, or any fragments or variants thereof, wherein said promoter is operably linked to a transcribable polynucleotide molecule.

In yet another embodiment, the present invention provides a transgenic plant stably transformed with a plant expression construct comprising a promoter provided by the invention. In one embodiment, the construct comprises a polynucleotide sequence substantially homologous to a polynucleotide sequence selected from the group consisting of SEQ ID NOs: 7, 8, and 9, or any fragments, variants, or regions thereof, wherein said promoter is operably linked to a transcribable polynucleotide molecule.

In another embodiment, the present invention provides a method of making a vegetable oil, comprising the steps of incorporating into the genome of a plant a promoter of the present invention operably linked to a transcribable polynucleotide molecule conferring altered oil and/or protein content, growing the plant to produce seeds, and extracting the oil and/or protein from the seed. In yet another embodiment, the invention provides a method for making food or feed comprising obtaining a plant of the invention and preparing the food or feed from the plant or a part thereof.

The foregoing and other aspects of the present invention will become more apparent from the following detailed description.

BRIEF DESCRIPTION OF THE SEQUENCES

SEQ ID NO: 1 sets forth the polynucleotide sequence for the P-BN.RPC-0:1:1 promoter.

SEQ ID NO: 2 sets forth the polynucleotide sequence for the primer GSP1.

SEQ ID NO: 3 sets forth the polynucleotide sequence for the primer AP1.

SEQ ID NO: 4 sets forth the polynucleotide sequence for the primer GSP2.

SEQ ID NO: 5 sets forth the polynucleotide sequence for the primer AP2.

SEQ ID NO: 6 sets forth the polynucleotide sequence for the primer D11 nco.

SEQ ID NO: 7 sets forth the polynucleotide sequence for the P-BN.SW1-0:1:2 promoter.

SEQ ID NO: 8 sets forth the polynucleotide sequence for the P-BN.SW2-0:1:2 promoter.

SEQ ID NO: 9 sets forth the polynucleotide sequence for the P-BN.SW3-0:1:2 promoter.

SEQ ID NO: 10 sets forth the polynucleotide sequence for the primer #17637.

SEQ ID NO: 11 sets forth the polynucleotide sequence for the primer #17636.

SEQ ID NO: 12 sets forth the polynucleotide sequence for the primer #17669.

SEQ ID NO: 13 sets forth the polynucleotide sequence for the primer #17668.

SEQ ID NO: 14 sets forth the polynucleotide sequence for the primer #18210.

SEQ ID NO: 15 sets forth the polynucleotide sequence for the primer #18209.

SEQ ID NO: 16 sets forth the polynucleotide sequence for the primer #18115.

SEQ ID NO: 17 sets forth the polynucleotide sequence for the primer #18167.

SEQ ID NO: 18 sets forth the polynucleotide sequence for the primer #18206.

SEQ ID NO: 19 sets forth the polynucleotide sequence for the primer #18340.

SEQ ID NO: 20 sets forth the polynucleotide sequence for the primer #19944.

SEQ ID NO: 21 sets forth the polynucleotide sequence for the primer #19945.

SEQ ID NO: 22 sets forth the polynucleotide sequence of the 891 bp fragment containing P-BN.SW3-0:1:2.

DETAILED DESCRIPTION OF THE INVENTION

The following definitions and methods are provided to better define the present invention and to guide those of ordinary skill in the art in the practice of the present invention. Unless otherwise noted, terms are to be understood according to conventional usage by those of ordinary skill in the relevant art.

As used herein, the phrase "polynucleotide molecule" refers to the single- or double-stranded DNA or RNA of genomic or synthetic origin, i.e., a polymer of deoxyribonucleotide or ribonucleotide bases, respectively, read from the 5' (upstream) end to the 3' (downstream) end.

As used herein, the phrase "polynucleotide sequence" refers to the sequence of a polynucleotide molecule. The nomenclature for DNA bases as set forth at 37 CFR §1.822 is used.

Promoters

As used herein, the term "promoter" refers to a polynucleotide molecule that in its native state is located upstream or 5' to a translational start codon of an open reading frame (or protein-coding region) and that is involved in recognition and binding of RNA polymerase II and other proteins (transacting transcription factors) to initiate transcription. A "plant promoter" is a native or non-native promoter that is functional in plant cells. Constitutive plant promoters are functional in most or all tissues of a plant throughout plant development. Any plant promoter can be used as a 5' regulatory element for modulating expression of a particular gene or genes operably associated thereto. When operably linked to a transcribable polynucleotide molecule, a promoter typically causes the transcribable polynucleotide molecule to be transcribed in a manner that is similar to that of which the promoter is normally associated. Plant promoters can include promoters produced through the manipulation of known promoters to produce artificial, chimeric, or hybrid promoters. Such promoters can also combine cis-elements from one or more promoters, for example, by adding a heterologous regulatory element to an active promoter with its own partial or complete regulatory elements. Thus, the design, construction, and use of chimeric or hybrid promoters comprising at least one cis-element of SEQ ID NOs: 7, 8, and 9 for modulating the expression of operably linked polynucleotide sequences is encompassed by the present invention.

As used herein, the term "cis-element" refers to a cis-acting transcriptional regulatory element that confers an aspect of the overall control of gene expression. A cis-element may function to bind transcription factors, trans-acting protein factors that regulate transcription. Some cis-elements bind more than one transcription factor, and transcription factors may interact with different affinities with more than one cis-element. The promoters of the present invention desirably contain cis-elements that can confer or modulate gene expression. Cis-elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of a cis-element can be further studied by mutagenesis (or substitution) of one or more nucleotides or by other conventional methods. Cis-elements can be obtained by chemical synthesis or by isolation from promoters that include such elements, and they can be synthesized with additional flanking nucleotides that contain useful restriction enzyme sites to facilitate subsequence manipulation.

In one embodiment, the promoters of the present invention comprise multiple cis-elements each of which confers a different aspect to the overall control of gene expression. In a preferred embodiment, cis-elements from the polynucleotide molecules of SEQ ID NOs: 7, 8, and 9, are identified using computer programs designed specifically to identify cis-element, domains, or motifs within sequences. Cis-elements may either positively or negatively regulate gene expression, depending on the conditions. The present invention therefore encompasses cis-elements of the disclosed promoters.

As used herein, the phrase "substantially homologous" refers to polynucleotide molecules that generally demonstrate a substantial percent sequence identity with the promoters provided herein. Of particular interest are polynucleotide molecules wherein the polynucleotide molecules function in plants to direct transcription and have at least about 70% sequence identity, at least about 80% sequence identity, at least about 90% sequence identity, or even greater sequence identity, specifically including about 73%, 75%, 78%, 83%, 85%, 88%, 92%, 94, 95%, 96%, 97%, 98%, 99% or greater sequence identity with the polynucleotide sequences of the promoters described herein, for example, provided in SEQ ID NO:7, SEQ ID NO:8 and SEQ ID NO:9. Polynucleotide molecules that are capable of regulating transcription of operably linked transcribable polynucleotide molecules and are substantially homologous to the polynucleotide sequences of the promoters provided herein are encompassed within the scope of this invention.

As used herein, the phrase "percent sequence identity" refers to the percentage of identical nucleotides in a linear polynucleotide sequence of a reference polynucleotide molecule (or its complementary strand) as compared to a test polynucleotide molecule (or its complementary strand) when the two sequences are optimally aligned (with appropriate nucleotide insertions, deletions, or gaps totaling less than 20% of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Acceirys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction times 100. The comparison of one or more polynucleotide sequences may be to a full-length polynucleotide sequence or a portion thereof, or to a longer polynucleotide sequence.

As used herein, the term "homology" refers to the level of similarity or percent identity between polynucleotide sequences in terms of percent nucleotide positional identity, i.e., sequence similarity or identity. As used herein, the term homology also refers to the concept of similar functional properties among different polynucleotide molecules, e.g., promoters that have similar function may have homologous cis-elements. Polynucleotide molecules are homologous when under certain conditions they specifically hybridize to form a duplex molecule. Under these conditions, referred to as stringency conditions, one polynucleotide molecule can be used as a probe or primer to identify other polynucleotide molecules that share homology. The phrase "stringent conditions" is functionally defined with regard to the hybridization of a nucleic-acid probe to a target nucleic acid (i.e., to a particular nucleic-acid sequence of interest) by the specific hybridization procedure discussed in Sambrook et al. (2000). Accordingly, the nucleotide sequences of the present invention may be used for their ability to selectively form duplex molecules with complementary stretches of polynucleotide molecule fragments.

Depending on the application envisioned one may desire to employ varying conditions of hybridization to achieve varying degrees of selectivity of probe towards target sequence. For applications requiring high selectivity, one will typically desire to employ relatively high stringent conditions to form the hybrids, e.g., one will select relatively low salt and/or high temperature conditions, such as provided by about 0.02 M to about 0.15 M NaCl at temperatures of about 50° C. to about 70° C. A high stringent condition, for example, is to wash the hybridization filter at least twice with high-stringency wash buffer (0.2×SSC, 0.1% SDS, 65° C.). Appropriate moderate stringency conditions that promote DNA hybridization, for example, 6.0×sodium chloride/sodium citrate (SSC) at about 45° C., followed by a wash of 2.0×SSC at 50° C., are known to those skilled in the art. Additionally, the salt concentration in the wash step can be selected from a low stringency of about 2.0×SSC at 50° C. to a high stringency of about 0.2× SSC at 50° C. Additionally, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little mismatch between the probe and the template or target strand. Detection of polynucleotide molecules via hybridization is well known to those of skill in the art, and the teachings of U.S. Pat. Nos. 4,965,188 and 5,176,995 are exemplary of the methods of hybridization analyses.

Homology can also be determined by computer programs that align polynucleotide sequences and estimate the ability of polynucleotide molecules to form duplex molecules under certain stringency conditions. Polynucleotide molecules from different sources that share a high degree of homology are referred to as "homologues".

Methods well known to one skilled in the art may be used to identify promoters of interest having activity similar to the promoters described herein. For example, cDNA libraries may be constructed using cells or tissues of interest and screened to identify genes having an expression pattern similar to that of the promoters described herein. The cDNA sequence for the identified gene may then be used to isolate the gene's promoter for further characterization. See, for example U.S. Pat. Nos. 6,096,950; 5,589,583; and 5,898,096, incorporated herein by reference. Alternately, transcriptional profiling or electronic northern techniques may be used to identify genes having an expression pattern similar to that of the promoters described herein. Once these genes have been identified, their promoters may be isolated for further characterization. See, for example U.S. Pat. Nos. 6,506,565 and 6,448,387, incorporated herein by reference. The electronic northern technique refers to a computer-based sequence analysis which allows sequences from multiple cDNA libraries to be compared electronically based on parameters the researcher identifies including abundance in EST populations in multiple cDNA libraries, or exclusively to EST sets from one or combinations of libraries. The transcriptional profiling technique is a high-throughput method used for the systematic monitoring of gene expression profiles for thousands of genes. This DNA chip-based technology arrays thousands of cDNA sequences on a support surface. These arrays are simultaneously hybridized to a population of labeled cDNA probes prepared from RNA samples of different cell or tissue types, allowing direct comparative analysis of expression. This approach may be used for the isolation of regulatory sequences such as promoters associated with those genes.

In another embodiment, the promoter disclosed herein can be modified. Those skilled in the art can create promoters that have variations in the polynucleotide sequence. The polynucleotide sequences of the promoters of the present invention as shown in SEQ ID NOs: 7, 8, and 9 may be modified or altered to enhance their control characteristics. One preferred method of alteration of a polynucleotide sequence is to use PCR to modify selected nucleotides or regions of sequences. These methods are well known to those of skill in the art. Sequences can be modified, for example by insertion, deletion, or replacement of template sequences in a PCR-based DNA modification approach. In the context of the present invention, a "variant" is a promoter containing changes in which one or more nucleotides of an original promoter is deleted, added, and/or substituted, preferably while substantially maintaining promoter function. For example, one or more base pairs may be deleted from the 5' or 3' end of a promoter to produce a "truncated" promoter. One or more base pairs can also be inserted, deleted, or substituted internally to a promoter. In the case of a promoter fragment, variant promoters can include changes affecting the transcription of a minimal promoter to which it is operably linked. A minimal or basal promoter is a polynucleotide molecule that is capable of recruiting and binding the basal transcription machinery. One example of basal transcription machinery in eukaryotic cells is the RNA polymerase II complex and its accessory proteins. Variant promoters can be produced, for example, by standard DNA mutagenesis techniques or by chemically synthesizing the variant promoter or a portion thereof.

Novel chimeric promoters can be designed or engineered by a number of methods. Many promoters contain cis-elements that activate, enhance, or define the strength and/or specificity of the promoter. For example promoters may contain "TATA" boxes defining the site of transcription initiation and other cis-elements located upstream of the transcription initiation site that modulate transcription levels. For example, a chimeric promoter may be produced by fusing a first promoter fragment containing the activator cis-element from one promoter to a second promoter fragment containing the activator cis-element from another promoter; the resultant chimeric promoter may cause an increase in expression of an operably linked transcribable polynucleotide molecule. Promoters can be constructed such that promoter fragments or elements are operably linked, for example, by placing such a fragment upstream of a minimal promoter. The cis-elements and fragments of the present invention can be used for the construction of such chimeric promoters. Methods for construction of chimeric and variant promoters of the present invention include, but are not limited to, combining control elements of different promoters or duplicating portions or regions of a promoter (see, for example, U.S. Pat. Nos. 4,990,607; 5,110,732; and 5,097,025, all of which are herein incorporated by reference). Those of skill in the art are familiar with the standard resource materials that describe specific conditions and procedures for the construction, manipulation, and isolation of macromolecules (e.g., polynucleotide molecules, plasmids, etc.), as well as the generation of recombinant organisms and the screening and isolation of polynucleotide molecules.

In another embodiment, a promoter comprising the polynucleotide sequence shown in SEQ ID NOs: 7, 8, and 9 includes any length of said polynucleotide sequence that is capable of regulating an operably linked transcribable polynucleotide molecule. For example, the promoters as disclosed in SEQ ID NOs: 7, 8, and 9 may be truncated or portions deleted and still be capable of regulating transcription of an operably linked polynucleotide molecule. In a related embodiment, a cis-element of the disclosed promoters may confer a particular specificity such as conferring enhanced expression of operably linked polynucleotide molecules in certain tissues and therefore is also capable of regulating transcription of operably linked polynucleotide molecules. Consequently, any fragments, portions, or regions of the promoters comprising the polynucleotide sequence shown in SEQ ID NOs: 7, 8, and 9 can be used as regulatory polynucleotide molecules, including but not limited to cis-elements or motifs of the disclosed polynucleotide molecules. Substitutions, deletions, insertions, or any combination thereof can be combined to produce a final construct.

Polynucleotide Constructs

As used herein, the phrase "polynucleotide construct" refers to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner. The terms "polynucleotide construct" and "construct" are used interchangeably herein.

As used herein, the phrase "operably linked" refers to a first polynucleotide molecule, such as a promoter, connected with a second transcribable polynucleotide molecule, such as a gene of interest, where the polynucleotide molecules are so arranged that the first polynucleotide molecule affects the function of the second polynucleotide molecule. Preferably, the two polynucleotide molecules are part of a single contiguous polynucleotide molecule and more preferably are adjacent. For example, a promoter is operably linked to a gene of interest if the promoter regulates or mediates transcription of the gene of interest in a cell.

As used herein, the phrase "transcribable polynucleotide molecule" refers to any polynucleotide molecule capable of being transcribed into an RNA molecule. Methods are known for introducing constructs into a cell in such a manner that the transcribable polynucleotide molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present invention, conventional compositions and methods for preparing and using constructs and host cells are well known to one skilled in the art, see for example, Sambrook et al.

Constructs of the present invention would typically contain a promoter operably linked to a transcribable polynucleotide molecule operably linked to a 3' transcription termination polynucleotide molecule. In addition, constructs may include but are not limited to additional regulatory polynucleotide molecules from the 3'-untranslated region (3' UTR) of plant genes (e.g., a 3' UTR to increase mRNA stability of the mRNA, such as the PI-II termination region of potato or the octopine or nopaline synthase 3' termination regions). Constructs may include but are not limited to the 5' untranslated regions (5' UTR) of an mRNA polynucleotide molecule which can play an important role in translation initiation and can also be a genetic component in a plant expression construct. For example, non-translated 5' leader polynucleotide molecules derived from heat shock protein genes have been demonstrated to enhance gene expression in plants (see, for example, U.S. Pat. Nos. 5,659,122 and 5,362,865; and U.S. Published Application No. 2002/0192812, herein incorporated by reference). These additional upstream and downstream regulatory polynucleotide molecules may be derived from a source that is native or heterologous with respect to the other elements present on the promoter construct.

Thus, constructs of the present invention comprise promoters such as those provided in SEQ ID NOs: 7, 8, and 9, or modified as described above, operatively linked to a transcribable polynucleotide molecule so as to direct transcription of said transcribable polynucleotide molecule at a desired level or in a desired tissue or developmental pattern upon introduction of said construct into a plant cell. In some cases, the transcribable polynucleotide molecule comprises a protein-coding region of a gene, and the promoter provides for transcription of a functional mRNA molecule that is translated and expressed as a protein product. Constructs may also be constructed for transcription of antisense RNA molecules or other similar inhibitory RNA in order to inhibit expression of a specific RNA molecule of interest in a target host cell.

Exemplary transcribable polynucleotide molecules for incorporation into constructs of the present invention include, for example, DNA molecules or genes from a species other than the target gene species, or even genes that originate with or are present in the same species, but are incorporated into recipient cells by genetic engineering methods rather than classical reproduction or breeding techniques. Exogenous gene or genetic element is intended to refer to any gene or DNA molecule that is introduced into a recipient cell. The type of DNA included in the exogenous DNA can include DNA that is already present in the plant cell, DNA from another plant, DNA from a different organism, or a DNA generated externally, such as a DNA molecule containing an antisense message of a gene, or a DNA molecule encoding an artificial or modified version of a gene.

The promoters of the present invention can be incorporated into a construct using marker genes as described and tested in transient analyses that provide an indication of gene expression in stable plant systems. As used herein the phrase "marker gene" refers to any transcribable polynucleotide molecule whose expression can be screened for or scored in some way. Methods of testing for marker gene expression in transient assays are known to those of skill in the art. Transient expression of marker genes has been reported using a variety of plants, tissues, and DNA delivery systems. For example, types of transient analyses can include but are not limited to direct gene delivery via electroporation or particle bombardment of tissues in any transient plant assay using any plant species of interest. Such transient systems would include but are not limited to electroporation of protoplasts from a variety of tissue sources or particle bombardment of specific tissues of interest. The present invention encompasses the use of any transient expression system to evaluate promoters or promoter fragments operably linked to any transcribable polynucleotide molecules, including but not limited to selected reporter genes, marker genes, or genes of agronomic interest. Examples of plant tissues envisioned to test in transients via an appropriate delivery system would include but are not limited to leaf base tissues, callus, cotyledons, roots, endosperm, embryos, floral tissue, pollen, and epidermal tissue.

Any scorable or screenable marker gene can be used in a transient assay. Preferred marker genes for transient analyses of the promoters or promoter fragments of the present invention include a GUS gene (U.S. Pat. No. 5,599,670, herein incorporated by reference) or a GFP gene (U.S. Pat. No. 5,491,084, herein incorporated by reference). The constructs containing the promoters or promoter fragments operably linked to a marker gene are delivered to the tissues and the tissues are analyzed by the appropriate mechanism, depending on the marker. The quantitative or qualitative analyses are used as a tool to evaluate the potential expression profile of the promoters or promoter fragments when operatively linked to genes of agronomic interest in stable plants.

Thus, in one preferred embodiment, a polynucleotide molecule of the present invention as shown in SEQ ID NOs: 7, 8, or 9, or fragments, variants, or derivatives thereof, capable of regulating transcription, is operably linked to a transcribable polynucleotide molecule that provides for a selectable, screenable, or scorable marker. Markers for use in the practice of the present invention include, but are not limited to transcribable polynucleotide molecules encoding β-glucuronidase (GUS), green fluorescent protein (GFP), luciferase (LUC), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep), and gentamycin (aac3 and aacC4) are known in the art. Herbicides for which transgenic plant tolerance has been demonstrated and the method of the present invention can be applied, include but are not limited to: glyphosate, glufosinate, sulfonylureas, imidazolinones, bromoxynil, delapon, cyclohezanedione, protoporphyrionogen oxidase inhibitors, and isoxasflutole herbicides. Polynucleotide molecules encoding proteins involved in herbicide tolerance are known in the art, and include, but are not limited to a polynucleotide molecule encoding 5-enolpyruvylshikimate-3-phosphate synthase (EPSP synthase) described in U.S. Pat. Nos. 5,627,061; 5,633,435; and 6,040,497; and aroA described in U.S. Pat. No. 5,094,945 for glyphosate tolerance; a polynucleotide molecule encoding bromoxynil nitrilase (Bxn) described in U.S. Pat. No. 4,810,648 for Bromoxynil tolerance; a polynucleotide molecule encoding phytoene desaturase (crtI) described in Misawa et al. (1993) and Misawa et al. (1994) for norflurazon tolerance; a polynucleotide molecule encoding acetohydroxyacid synthase (AHAS, aka ALS) described in Sathasiivan et al. (1990) for tolerance to sulfonylurea herbicides; and the bar gene described in DeBlock et al. (1987) for glufosinate and bialaphos tolerance.

In one preferred embodiment, a polynucleotide molecule of the present invention as shown in SEQ ID NOs: 7, 8, or 9, or fragments, variants, or derivatives thereof, capable of regulating transcription, is operably linked to a transcribable polynucleotide molecule that is a gene of agronomic interest. As used herein, the phrase "gene of agronomic interest" refers to a transcribable polynucleotide molecule that includes but is not limited to a gene that provides a desirable characteristic associated with plant morphology, physiology, growth and development, yield, nutritional enhancement, disease or pest resistance, or environmental or chemical tolerance. The expression of a gene of agronomic interest is desirable in order to confer an agronomically important trait. A gene of agronomic interest that provides a beneficial agronomic trait to crop plants may be, for example, including, but not limited to genetic elements comprising herbicide resistance (U.S. Pat. Nos. 5,633,435 and 5,463,175), increased yield (U.S. Pat. No. 5,716,837), insect control (U.S. Pat. Nos. 6,063,597; 6,063,756; 6,093,695; 5,942,664; and 6,110,464), fungal disease resistance (U.S. Pat. Nos. 5,516,671; 5,773,696; 6,121,436; 6,316,407; and 6,506,962), virus resistance (U.S. Pat. Nos. 5,304,730 and 6,013,864), nematode resistance (U.S. Pat. No. 6,228,992), bacterial disease resistance (U.S. Pat. No. 5,516,671), starch production (U.S. Pat. Nos. 5,750,876 and 6,476,295), modified oils production (U.S. Pat. No. 6,444,876), high oil production (U.S. Pat. Nos. 5,608,149 and 6,476,295), modified fatty acid content (U.S. Pat. No. 6,537,750), high protein production (U.S. Pat. No. 6,380,466), fruit ripening (U.S. Pat. No. 5,512,466), enhanced animal and human nutrition (U.S. Pat. Nos. 5,985,605 and 6,171,640), biopolymers (U.S. Pat. No. 5,958,745 and U.S. Published Application No. 2003/0028917), environmental stress resistance (U.S. Pat. No. 6,072,103), pharmaceutical peptides (U.S. Pat. No. 6,080,560), improved processing traits (U.S. Pat. No. 6,476,295), improved digestibility (U.S. Pat. No.

6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), and biofuel production (U.S. Pat. No. 5,998,700), the genetic elements and transgenes described in the patents listed above are herein incorporated by reference.

Alternatively, a transcribable polynucleotide molecule can affect the above mentioned phenotypes by encoding a non-translatable RNA molecule that causes the targeted inhibition of expression of an endogenous gene, for example via anti-sense, RNAi, or cosuppression-mediated mechanisms. The RNA could also be a catalytic RNA molecule (i.e., a ribozyme) engineered to cleave a desired endogenous mRNA product. Thus, any polynucleotide molecule that encodes a protein or mRNA that expresses a phenotype or morphology change of interest is useful for the practice of the present invention.

The constructs of the present invention may in one embodiment be double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *Agrobacterium* cells, permits the integration of the T-DNA into the genome of a plant cell. The constructs also may contain the plasmid backbone DNA segments that provide replication function and antibiotic selection in bacterial cells, for example, an *E. coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, or LBA4404, however, other strains known to those skilled in the art of plant transformation can function in the present invention.

Transformed Plants And Plant Cells

As used herein, the term "transformed" refers to a cell, tissue, organ, or organism into which has been introduced a foreign polynucleotide molecule, such as a construct. Preferably, the introduced polynucleotide molecule is integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic plant as a parent in a cross and exhibiting an altered phenotype resulting from the presence of a foreign polynucleotide molecule. A plant transformation construct containing a promoter of the present invention may be introduced into plants by any plant transformation method. Methods and materials for transforming plants by introducing a plant expression construct into a plant genome in the practice of this invention can include any of the well-known and demonstrated methods including electroporation as illustrated in U.S. Pat. No. 5,384,253; microprojectile bombardment as illustrated in U.S. Pat. Nos. 5,015,580; 5,550,318; 5,538,880; 6,160,208; 6,399,861; and 6,403,865; *Agrobacterium*-mediated transformation as illustrated in U.S. Pat. Nos. 5,635,055; 5,824,877; 5,591,616; 5,981,840; and 6,384,301; and protoplast transformation as illustrated in U.S. Pat. No. 5,508,184, all of which are incorporated herein by reference.

Methods for specifically transforming dicots are well known to those skilled in the art. Transformation and plant regeneration using these methods have been described for a number of crops including, but not limited to, soybean (*Glycine max*), *Brassica* sp., *Arabidopsis thaliana*, cotton (*Gossypium hirsutum*), peanut (*Arachis hypogae*), sunflower (*Helianthus annuus*), potato (*Solanum tuberosum*), tomato (*Lycopersicon esculentum* L.), and alfalfa (*Medicago sativa*). It is apparent to those of skill in the art that a number of transformation methodologies can be used and modified for production of stable transgenic plants from any number of target crops of interest.

In another embodiment, the present invention provides a method of making a vegetable oil, comprising the steps of incorporating into the genome of a plant a promoter of the present invention operably linked to a transcribable polynucleotide molecule conferring altered oil and/or protein content, growing the plant to produce seeds, and extracting the oil and/or protein from the seed.

The transformed plants may be analyzed for the presence of the genes of interest and the expression level and/or profile conferred by the promoters of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays.

The seeds of this invention can be harvested from fertile transgenic plants and be used to grow progeny generations of transformed plants of this invention. The terms "seeds" and "kernels" are understood to be equivalent in meaning. In the context of the present invention, the seed refers to the mature ovule consisting of a seed coat, embryo, aleurone, and an endosperm.

The phrase "cell proliferation" refers to cells undergoing mitotic cell divisions, such as in rapidly growing tissues.

The phrase "micronutrient content" means the amount of micronutrients, i.e., vitamins or carotenoids, within a seed expressed on a per weight basis.

The phrase "oil content" means the concentration of the oil fraction, expressed as a weight percentage or parts per million basis, which may be determined, for example, by low-resolution $^1$H nuclear magnetic resonance (NMR) (Tiwari et al., 1974) or Rubel, 1994) or near infrared transmittance (NIT) spectroscopy (Orman et al., 1992; Patrick et al., 1997).

The phrase "protein quality" means the level of one or more essential amino acids, whether free or incorporated in protein, namely histidine, isoleucine, leucine, lysine, methionine, cysteine, phenylalanine, tyrosine, threonine, tryptophan, and valine.

The following examples are included to demonstrate preferred embodiments of the present invention. It should be appreciated by those of skill in the art that the techniques disclosed in the examples that follow represent techniques discovered by the inventors to function well in the practice of the present invention. However, those of skill in the art should, in light of the present disclosure, appreciate that many changes can be made in the specific embodiments that are disclosed and still obtain a like or similar result without departing from the spirit and scope of the present invention, therefore all matter set forth or shown in the accompanying drawings is to be interpreted as illustrative and not in a limiting sense.

EXAMPLE 1

This example describes the identification and isolation of expressed sequence tags (ESTs) from *Brassica napus*, using an electronic library subtraction method. Proprietary *B. napus* EST libraries were used as the target tissue and proprietary *Arabidopsis* and *B. napus* cDNA libraries as the background tissue. ESTs identified as potentially being expressed only in the silique tissue were further characterized by hybridization.

EST Library Construction

The target tissue EST Library was constructed from a variety of tissues isolated from greenhouse grown *Brassica napus* (cultivar Quantum). The isolated tissues included: silique walls at 10, 20, 30, 40, and 50 days after pollination (DAP), aleurone and seed coat at 25-28 DAP. Tissues were flash frozen in liquid nitrogen and stored at −70° C. prior to RNA extraction. RNA was extracted by grinding approximately 500 mg plant tissue in liquid nitrogen with a mortar and pestle. The ground tissue was mixed with 5 ml REC.8+ (Tris-HCl, pH9, 0.8 M NaCl, 10 mM EDTA, 0.5% β-mercaptoethanol, and 0.5% cetyltrimethyl-ammonium bromide) plus 0.1 g of polyvinylpolypyrrolidone. The mixture was homogenized with a mortar and pestle and was centrifuged at 5000 g for 5 minutes. The aqueous phase was extracted once with 1.5 ml phenol:chloroform (1:1, v/v) and once with 1.5 ml chloroform. RNA was precipitated from the aqueous layer with an equal volume of 95% ethanol and pelleted at 10,000×g for 20 minutes. Precipitated RNA was resuspended in water and one volume of 8 M LiCl were added. The mixture was incubated at −20° C. for 1 hour, followed by centrifugation at 10,000×g for 20 minutes. Precipitated RNA was washed with 70% ethanol, air dried, and dissolved in water treated with diethylpyrocarbonate (DEPC water). Approximately 25 µg of total RNA was used to prepare double-stranded cDNA using the SuperScript Plasmid System (Invitrogen Corporation Carlsbad, Calif.) according to the manufacturer's protocol.

EST sequences were generated for each of the six libraries described above. Candidate sequences were identified by using the EST sequences from each library as a query against Monsanto proprietary *Arabidopsis* and *Brassica napus* cDNA libraries and the public GenBank® cDNA collection. GenBank® is the NIH genetic sequence database, an annotated collection of all publicly available DNA sequences. The most highly expressed genes from each library were identified by determining the frequency of appearance in all cDNA collections. An additional BLAST search was completed to identify clones specific for each library.

A second bioinformatics screen was then done using a proprietary Library Subtraction Program. The six libraries described above were used as target libraries. All available Monsanto proprietary, non-silique wall *Brassica napus* cDNA libraries were used as background libraries. The sequences that were present in any of the target libraries but not present in any of the background libraries, were identified as meeting the criteria for further investigation. The 200 most abundant messages meeting these criteria were characterized further. Fifteen sequences were eliminated for overlap with the initial screen. An additional seven sequences were eliminated for significant identity with retrotransposons. The remaining sequences were then BLAST searched against *Arabidopsis* cDNA libraries derived from leaf, root, stem, flower bud, open flower, and developing seed. Eighty-nine of these sequences were eliminated from consideration for having significant identity to non-silique wall sequences. The remaining 89 EST clones were thus identified from this screening and were further investigated by hybridization screening.

Hybridization Screening

The EST sequences identified above were digested with SalI and NotI to release the insert. Fragments were separated on 0.8% agarose gels in 1×TBE. To facilitate transfer, the gels were exposed to short wave uv light for 2-3 minutes. The DNA was denatured in 0.5 N NaOH; 1.5 M NaCl and transferred to Nytran Plus (Schleicher & Schuell BioScience, Dassel, Germany) using the TurboBlotter system (Schleicher & Schuell). Blots were hybridized to radiolabelled cDNA derived from silique walls at 10, 20, 30, 40, and 50 DAP, aleurone/seed coat, developing embryo (15-18 DAP), floral buds, open flower, leaf, and root using the SMART cDNA PCR amplification Kit (BD Biosciences, Franklin Lakes, N.J.) according to manufacturer's instructions with the addition of radiolabelled dCTP to the final PCR reaction. A number of the clones were eliminated due to hybridization to cDNAs that were derived from developing embryo (15-18 DAP), floral buds, open flower, leaf, and/or root. The remaining 67 clones were used as probes against SMART™ cDNAs (BD Biosciences) derived RNA isolated from silique walls at 10, 15, 20, 25, 30, 35, 40, 45, and 50 DAP, aleurone/seed coat, developing embryo (15-18 DAP), floral buds, open flower, leaf, and root. Six candidates hybridized predominantly to silique wall and/or aleurone. One clone hybridized specifically to root derived cDNA.

Clone LIB4156-008-R1-K1-A4 was characterized as being expressed in the root cells. Clone LIB4153-003-R1-K9-C1 was characterized as being expressed in silique wall, aleurone/seed coat, and open flower. Clone LIB4156-012-R1-K1-D2 was characterized as being expressed in silique wall, aleurone/seed coat, and root. Clone LIB4153-011-R1-K1-E3 was characterized as being expressed in silique wall, aleurone/seed coat, and open flower. Clone LIB4169-011-Q1-K1-G2 was characterized as being expressed in aleurone/seed coat. Clone LIB4169-008-Q1-K1-D8 was characterized as being expressed in silique wall, aleurone/seed coat, and developing embryo. Clones LIB4153-003-R1-K9-C1, LIB4156-012-R1-K1-D2, LIB4153-011-R1-K1-E3, and LIB4156-008-R1-K1-A4 were submitted for sequence confirmation. All but clone LIB4156-008-R1-K1-A4 were verified as being the expected sequence. The correct clone designation for LIB4156-008-R1-K1-A4 was determined to be LIB4156-011-R1-K1-C3.

EXAMPLE 2

This example describes the isolation of promoter sequences from *Brassica napus* using the EST sequences identified above.

Genome Walker Library Preparation

*Brassica napus* leaves were harvested and kept frozen in liquid nitrogen until extraction. The tissue was ground to a fine powder using a mortar and pestle while keeping the tissue frozen with liquid nitrogen. Approximately 0.4 grams of ground tissue was transferred to a centrifuge tube. Six milliliters of 65° C. SDS extraction buffer (1 M Tris; 0.25 M EDTA; pH 8.0 with HCL; 20% SDS; 5 M NaCl β-mercaptoethanol (7.1:10)) was added just before use. The mixture was vortexed vigorously for 30-60 seconds. Samples were then incubated at 65° C. for 45 minutes, with inversion every 15 minutes. Two milliliters of ice temperature 5 M potassium acetate solution was added, the samples were inverted gently to mix, and then incubated on ice for 20 minutes. The samples were chloroform extracted by adding 3 mls of chloroform to each tube and shaking gently for 10 minutes. The samples were then centrifuged at 9,000 RPM for 20 minutes. The supernatant was filtered through a layer of miracloth and collected in a clean centrifuge tube. The DNA was precipitated by adding 2 ml of 100% isopropanol gently mixed by inverting the tubes 3-4 times, and then centrifuging at 9,000 RPM for 20 minutes. The isopropanol was poured off, and the pellet was resuspended in 200 µl RNAseA solution (1 µl of a 100 mg/ml stock from Qiagen Inc., Valencia, Calif., diluted in 1 ml 50 mM Tris-HCL; 10 mM EDTA). A volume of 300 µl of ammonium acetate/100% isopropanol (1:7) was added. Samples were vortexed and spun at 9,000 RPM for 15 minutes. Resulting supernatant was poured off, and the pellet was washed with 500 µl of 80% ethanol. The ethanol was gently decanted and the pellet was allowed to air dry on the bench top. The pellet was resuspended in approximately 200 µl TE Buffer (10 mM Tris-HCL pH8, 1 mM EDTA). The resulting DNA was used to prepare Genome Walker™ libraries following the manufacturer's recommended protocol (Clontech, Palo Alto, Calif.).

The P-BN.RPC-0:1:1 root preferred promoter sequence [SEQ ID NO: 1] was isolated from the Genome Walker™ libraries described above. Primers were designed using the manufacturer's parameters for length, melting temperature (Tm), and sequence composition, from the available EST sequence of clone LIB4156-011-R1-K1-C3. A first round PCR reaction was run using the Genome Walker libraries as the template and the following primers:

```
GSP1
                                            [SEQ ID NO: 2]
5'-GCTACGGCGATGAGAAGAGAAATAAAATG-3',
and AP1
                                            [SEQ ID NO: 3]
5'-GTAATACGACTCACTATAGGGC-3'
(supplied by BD Biosciences).
```

The resulting amplification product was isolated using standard techniques well know in the art. A second PCR reaction was then performed using the first round amplification product as the template and the following primers:

```
GSP2
                                            [SEQ ID NO: 4]
5'-CCCACAGATTTTCTATTTCGGTTCTCATAC-3',
and AP2
                                            [SEQ ID NO: 5]
5'-ACTATAGGGCACGCGTGGT-3'
(supplied by BD Biosciences).
```

The product of the PCR reaction was purified according to standard methodology well known in the art and cloned into pCR2.1 Topo (Invitrogen Corporation, Carlsbad, Calif.) according to manufacturer's instructions. The resulting plasmid was named 2d11-2. The sequence of this clone was determined using standard sequencing methodologies as set forth by PE Applied Biosystems, (Foster City, Calif.). To facilitate further cloning, an NcoI site was added to the 3' end of the promoter fragment, following the PCR protocol recommended by the enzyme manufacturer (PE Applied Biosystems). Briefly, approximately 10 nanograms of plasmid 2d11-2 was used as the template and amplified using 30 nanomoles each of the following primers:

```
D11 nco (#18337)
                                            [SEQ ID NO: 6]
5'-GAGAAACCATGGTGAATAAATGG-3',
and API [SEQ ID NO: 3, described above].
```

Additionally, 10 micromoles each of dATP, dCTP, dGTP, and TTP, and 2.5 units of AmpliTaq Gold in 1× Opti-Prime™ Buffer 3 (Stratagene), were used in the reaction. After an initial incubation at 95° C. for 10 minutes, 25 cycles of PCR were performed with a cycle define as 92° C. for 30 seconds, 56° C. for 30 seconds, and 72° C. for 2 minutes, followed by 1 cycle of 72° C. for 7 minutes. The product of the PCR reaction was purified according to standard methodology well known in the art and cloned into pCR2.1 Topo (Invitrogen) according to manufacturer's instructions. The resulting plasmid was named pMON69833. The sequence of this clone was determined using standard sequencing methodologies as set forth by PE Applied Biosystems.

Isolation of P-BN.SW1-0:1:2, P-BN.SW2-0:1:2, and P-BN.SW3-0:1:2

The silique wall preferred promoter sequences, P-BN.SW1-0:1:2, P-BN.SW2-0:1:2, and P-BN.SW3-0:1:2 were isolated from the Genome Walker™ libraries using a procedure similar to that described above for P-BN.RPC-0:1:1 with the manufacturer's instruction. For the first round PCR reactions, primers were designed for each target sequence, using the manufacturer's parameters for length, Tm and sequence composition, from the respective EST sequences.

The table below shows the EST clones used as template DNA and the primers used for the first round PCR reactions in the isolation of the listed promoter sequences.

| Promoter | EST clone ID | Primer 1 | Primer 2 |
| --- | --- | --- | --- |
| P-BN.SW1-0:1:2 | LIB4153-003-R1-K9-C1 | #17637 | #17636 |
| P-BN.SW2-0:1:2 | LIB4156-012-R1-K1-D2 | #17669 | #17668 |
| P-BN.SW3-0:1:2 | LIB4153-011-R1-K1-E3 | #18210 | #18209 |

Primer Sequences

```
                                            [SEQ ID NO: 10]
#17637 5'-TTCATATCTGCGTAAGTACGTCCATGTTC-3'

[SEQ ID NO: 11]
#17636 5'-CGAGAAACAGAATGATGAAACTAGAGAGAC-3'

[SEQ ID NO: 12]
#17669 5'-CACCATGCTTTCACGTCTTTTGAGTTG-3'

[SEQ ID NO: 13]
#17668 5'-TCGATGCCACGAAAATGCATAAGAAC-3'

[SEQ ID NO: 14]
#18210 5'-CCTCATCCTCATCCTCATCCTCAACC-3'

[SEQ ID NO: 15]
#18209 5'-CCGTACACGGTAAAATAGTTCTTGACGGA-3'
```

A second amplification was then performed, similar to that described above for P-BN.RPC-0:1:1, using the first round amplification products from the respective reactions as the template, and the following primers:

| | |
|---|---|
| P-BN.SW1-0:1:1 | GSP2 [SEQ ID NO: 4] and AP2 [SEQ ID NO: 5] (supplied by the manufacturer), |
| P-BN.SW2-0:1:1 | GSP1 [SEQ ID NO: 2] and AP2 [SEQ ID NO: 5], |
| P-BN.SW3-0:1:1 | GSP2 [SEQ ID NO: 4] and AP2 [SEQ ID NO: 5]. |

The products of the respective PCR reactions were purified according to standard methodology well known in the art and cloned into pCR2.1 Topo (Invitrogen) according to manufacturer's instructions. The resulting plasmids were named 3d2-2, 3d3-46, and 4G5-1 for promoters P-BN.SW1-0:1:2, P-BN.SW2-0:1:2, and P-BN.SW3-0:1:2, respectively. The sequences for these clones were determined using standard sequencing methodologies as set forth by PE Applied Biosystems, (Foster City, Calif.).

Similar to the procedure described above for P-BN.RPC-0:1:1, an NcoI site was added to the 3' end of each promoter fragment to facilitate cloning. As described above, the reaction conditions for the PCR reactions followed the protocol recommended by the enzyme manufacturer (PE Applied Biosystems, Foster City, Calif.). The primers for the specific reactions were as follows:

```
Plasmid DNA 3d2-2 (P-BN.SW1-0:1:2)
                                    [SEQ ID NO: 16]
#18115 5'-CTAAAGCCATGGTCTTAGAAAAGTTG-3',
and

[SEQ ID NO: 17]
#18167 5'-AATACGACTCACTATAGGGCACGC-3';

Plasmid DNA 3d3-46 (P-BN.SW2-0:1:2)
                                    [SEQ ID NO: 18]
#518206 '-GAAAAGCCATGGTAAGGCCAATATT-3',
and AP1 [SEQ ID NO: 3]
Plasmid DNA 4G5-1 (P-BN.SW3-0:1:2)
                                    [SEQ ID NO: 19]
#18340 5'-CTTCTGCCATGGAAAGAAAAAGTTG-3',
and

AP1. [SEQ ID NO: 3]
```

The products of the PCR reactions were purified according to standard methodology well known in the art and cloned into pCR2.1 Topo (Invitrogen) according to manufacturer's instructions. The resulting plasmids were named pMON69828, pMON69829, and pMONM69830, containing the nucleic acid sequences for P-BN.SW1-0:1:2, P-BN.SW2-0:1:2, and P-BN.SW3-0:1:2, respectively. The sequences of these clones were determined using standard sequencing methodologies as set forth by PE Applied Biosystems.

EXAMPLE 3

This example describes the construction of plant transformation vectors containing the promoter sequences described above. The promoter sequences were linked to the marker gene, E. coli uidA, resulting in constructs designed to demonstrate expression in Arabidopsis and Canola.

PMON69832 (P-BN.RPC-0:1:1::GUS)

A 1661 bp fragment containing P-BN.RPC-0:1:1 [SEQ ID NO: 1] was removed from pMON69833 by digestion with SmaI and Nco I. The fragment was ligated into the plasmid pMON65425, which had also been digested with SmaI and NcoI. The resulting plasmid, containing P-BN.RPC-0:1:1 driving the E. coli uidA gene and with the napin 3' UTR was named pMON69832. The nucleic acid sequence was determined using known methodology and confirmed the integrity of the cloning junctions.

PMON69827 (P-BN.SW1-0:1:2::GUS)

A 1297 bp fragment containing P-BN.SW1-0:1:2 [SEQ ID NO: 7] was removed from pMON69828 by digestion with SmaI and Nco I. The fragment was ligated into the plasmid pMON65425, which had also been digested with SmaI and NcoI. The resulting plasmid, containing P-BN.SW1-0:1:2 driving the E. coli uidA gene and with the napin 3' UTR, was named pMON69827. The nucleic acid sequence was determined using known methodology and confirmed the integrity of the cloning junctions.

PMON69825 (P-BN.SW2-0:1:2::GUS)

A 854 bp fragment containing P-BN.SW2-0:1:2 [SEQ ID NO: 8] was removed from pMON69829 by digestion with SmaI and Nco I. The fragment was ligated into pMON65425, which had also been digested with SmaI and NcoI. The resulting plasmid, containing P-BN.SW2-0:1:2 driving the E. coli uidA gene and with the napin 3' UTR was named pMON69825. The nucleic acid sequence was determined using known methodology and confirmed the integrity of the cloning junctions.

PMON69831 (P-BN.SW3-0:1:2::GUS)

An 888 bp fragment containing P-BN.SW3-0:1:2 (SEQ ID NO: 9) was removed from pMON69830 by digestion with SmaI and Nco I. The fragment was ligated into pMON65425, which had also been digested with SmaI and NcoI. The resulting plasmid, containing P-BN.SW3-0:1:2 driving the E. coli uidA gene and with the napin 3' UTR was named pMON69831. The nucleic acid sequence was determined using known methodology and confirmed the integrity of the cloning junctions.

EXAMPLE 4

This example sets forth the procedure for transforming Arabidopsis plants with the vectors described above. Arabidopsis plants were grown by sowing seeds onto 4-inch pots containing reverse osmosis water (ROW) saturated Metro-Mix 200 (The Scotts Company, Columbus, Ohio). The plants were vernalized by placing the pots in a covered flat, in a growth chamber at 4-7° C., 8 hours light/day for 4-7 days. The flats were transferred to a growth chamber at 22° C., 55% relative humidity, and 16 hours light/day at an average intensity of 160-200 µEinstein/s/m$^2$. The cover was lifted and slid back 1-inch after germination, and removed when the true leaves had formed. The plants were bottom watered, as needed, with ROW until 2-3 weeks after germination. Plants were then bottom watered, as needed, with Plantex 15-15-18 solution (Plantex Corporation Ottawa, Canada) at 50 ppm N2. Pots were thinned such that 1 plant remained per pot at 2-3 weeks after germination. Once the plants began to bolt, the primary inflorescence was trimmed to encourage the growth of axillary bolts.

Transgenic Arabidopsis thaliana plants were obtained as described by Bent et al. (1994), or Bechtold et al. (1993).

Cultures of *Agrobacterium tumefaciens* strain ABI containing either one of the transformation vectors pMON69832, pMON69827, pMON69825, or pMON69831 were grown overnight in LB (10% bacto-tryptone, 5% yeast extract, and 10% NaCl with kanamycin (75 mg/L), chloramphenicol (25 mg/L), and spectinomycin (100 mg/L)). The bacterial culture was centrifuged and resuspended in 5% sucrose+0.05% Silwet-77 solution. The aerial portions of whole *Arabidopsis* plants (at about 5-7 weeks of age) were immersed in the resulting solution for 2-3 seconds. The excess solution was removed by blotting the plants on paper towels. The dipped plants were placed on their side in a covered flat and transferred to a growth chamber at 19° C. After 16 to 24 hours the dome was removed and the plants were set upright. When plants had reached maturity, water was withheld for 2-7 days prior to seed harvest. Harvested seed was passed through a stainless steel mesh screen (40 holes/inch) to remove debris. The harvested seed was then stored in paper coin envelopes at room temperature until analysis.

The seeds from the transgenic *Arabidopsis* plants were surfaced sterilized using a vapor phase sterilization protocol. Briefly, an open container of seeds was placed in a dessicator with a beaker containing 100 ml of household bleach. Immediately prior to sealing the dessicator, 3 ml concentrated HCl was added to the bleach solution to generate chlorine gas. The dessicator is sealed and a vacuum was applied to allow sterilization by chlorine fumes. The seeds were incubated for several hours. Sterilized seed were sprinkled onto *Arabidopsis* germination media [MS Salts (1×); sucrose (1%); myo-inositol (100 mg/L); thiamine-HCl (1 mg/L); pyridoxine-HCl (500 mg/L); nicotinic acid (500 mg/L); MES pH 5.7 (0.05%) and Phytagar (0.7%)] supplemented with 50 mg/L glyphosate. Up to 16 glyphosate resistant seedlings were transplanted to 2¼-inch pots containing MetroMix 200, thinned to one seedling per pot, and were grown under the conditions described above until the initial siliques that had formed began to desiccate. Tissue (rosette leaf, cauline leaf, stem, flowers, floral buds, and developing siliques) was removed from each T1 plant for subsequent histochemical staining.

Canola plants were transformed using the protocol described by Moloney and Radke in U.S. Pat. No. 5,720,871. Briefly, seeds of *Brassica napus* cv Ebony were planted in 2-inch pots containing Metro Mix 350 (The Scotts Company, Columbus, Ohio). The plants are grown in a growth chamber at 24° C., and a 16/8 hour photoperiod, with light intensity of 400 µEm-2 sec-1 (HID lamps). After 2½ weeks, the plants were transplanted into 6-inch pots and grown in a growth chamber at 15/10° C. day/night temperature, 16/8 hour photoperiod, light intensity of 800 µEm-2 sec-1 (HID lamps). Four terminal internodes from plants just prior to bolting or in the process of bolting but before flowering are removed and surface sterilized in 70% v/v ethanol for 1 minute, 2% w/v sodium hypochlorite for 20 minutes and rinsing 3 times with sterile deionized water. Six to seven stem segments are cut into 5 mm discs, maintaining orientation of basal end. Cultures of *Agrobacterium tumefaciens* strain ABI containing one of the transformation vectors pMON69832, pMON69827, pMON69825, or pMON69831 are grown overnight on a rotator shaker at 24° C. in 2 mls of Luria Broth, LB, (10% bacto-tryptone, 5% yeast extract, and 10% NaCl) containing 50 mg/l kanamycin, 24 mg/l chloramphenicol and 100 mg/l spectinomycin. A 1:10 dilution is made in MS media (Murashige and Skoog, 1962) giving approximately 9×10$^8$ cells per ml. The stem discs (explants) are inoculated with 1.0 ml of *Agrobacterium* and the excess is aspirated from the explants. The explants are placed basal side down in petri plates containing media comprising 1/10 MS salts, B5 vitamins (1% inositol; 0.1% thiamine HCl; 0.01% nicotinic acid; 0.01% pyridoxine-HCl), 3% sucrose, 0.8% agar, pH 5.7, 1.0 mg/l 6-benzyladenine (BA). The plates are layered with 1.5 ml of media containing MS salts, B5 vitamins, 3% sucrose, pH 5.7, 4.0 mg/l p-chlorophenoxyacetic acid, 0.005 mg/l kinetin and covered with sterile filter paper. Following a 2 to 3 day co-culture, the explants are transferred to deep dish petri plates containing MS salts, B5 vitamins, 3% sucrose, 0.8% agar, pH 5.7, 1 mg/l BA, 500 mg/l carbenicillin, 50 mg/l cefotaxime, and 25 mg/l glyphosate for selection. Seven explants are placed on each plate. After 3 weeks they are transferred to fresh media, 5 explants per plate. The explants are cultured in a growth room at 25° C., continuous light.

The transformed plants are grown in a growth chamber at 22° C. in a 16-8 hours light-dark cycle with light intensity of 220 µEm$^{-2}$ s$^{-1}$ for several weeks before transferring to the greenhouse. The plants are then grown in greenhouse conditions until maturity. The resulting mature R1 seeds are collected for analysis. Plants are maintained in a greenhouse under standard conditions. Developing seed is harvested at various stages after pollination and stored at negative 70° C. Mature seed is collected and stored under controlled conditions consisting of about 17° C. and 30% humidity.

EXAMPLE 5

This example describes the analysis of the expression of β-glucuronidase in *Arabidopsis thaliana* plants transformed with pMON69832, pMON69827, pMON69825, or pMON69831 using histochemical staining. The results of this analysis provide a characterization of the expression for the different promoters.

Freshly harvested tissues from transformed *Arabidopsis* plants were incubated for approximately 24 hours at 37° C. in a solution containing 50 mM NaPO$_4$ (pH 7.2); 100 µM potassium ferricyanide; 100 µM potassium ferrocyanide, 0.03% Triton X-100; 20% methanol and 2.5 mg/ml 5-bromo-4-chloro-3-indoyl glucuronic acid (X-gluc). In some cases the potassium ferricyanide, potassium ferrocyanide, and methanol were omitted from the staining solution. The stained tissue was cleared of chlorophyll by an overnight incubation in 70% ethanol/30% H$_2$O at 37° C. Stained tissues were photographed immediately or transferred to a solution of 70% ethanol/30% glycerol (v/v) and stored at 4° C. until photographed. The samples were then scored as positive (+) or negative (−) for staining a blue color.

For detection of expression in canola, up to 5 siliques were harvested from individual R0 plants at several time points after pollination. Siliques were scored with an 18 gauge needle to allow the staining solution to contact the developing seed. The siliques were incubated for approximately 24 hours at 37° C. in a solution containing 50 mM NaPO$_4$ (pH 7.2); 100 µM potassium ferricyanide; 100 µM potassium ferrocyanide, 0.03% Triton X-100; 20% methanol and 2.5 mg/ml 5-bromo-4-chloro-3-indoyl glucuronic acid (X-gluc). The stained tissue was cleared of chlorophyll by an overnight incubation in 70% ethanol/30% H$_2$O at 37° C. Stained tissues were photographed immediately or transferred to a solution of 70% ethanol/30% glycerol (v/v) and stored at 4° C. until photographed. Samples were scored positive (+) or negative (−) for blue color.

For P-BN.RPC-0:1:1, a root preferred promoter contained in pMON69832, none of 10 plants screened had detectable levels of activity in the silique wall (data not shown). For pMON69827, 3 out of 10 plants screened had detectable levels of activity in the silique wall from at least one time point. For pMON69825, 6 out of 10 plants screened had detectable levels of activity in the silique wall from at least one time point. For pMON69831, 5 out of 10 plants screened had detectable levels of activity in the silique wall from at least one time point. No activity was detected in the seed coat or aleurone of plants transformed with pMON69831. Time course data for individual transformants is presented in Tables 1-3.

TABLE 1

P-BN.SW1-0:1:2 Expression in Developing Canola Siliques

| | | Days After Pollination | | | | | | | | |
|---|---|---|---|---|---|---|---|---|---|---|
| Construct | Event | 3 | 6 | 9 | 12 | 15 | 20 | 25 | 30 | 35 | 40 |
| pMON69827 | BN_G1427 | − | − | − | − | − | − | − | − | − | − |
| pMON69827 | BN_G1428 | − | − | − | − | − | − | − | − | − | − |
| pMON69827 | BN_G1429 | − | − | − | − | − | − | − | − | − | − |
| pMON69827 | BN_G1430 | − | − | − | − | − | − | − | − | − | − |
| pMON69827 | BN_G1480 | − | − | − | − | − | − | − | − | − | − |
| pMON69827 | BN_G1481 | − | ND | − | ND | + | − | − | − | − | − |
| pMON69827 | BN_G1482 | − | − | − | + | − | + | − | − | − | + |
| pMON69827 | BN_G1507 | + | + | + | + | + | + | + | + | + | + |
| pMON69827 | BN_G1539 | − | − | − | − | − | − | − | − | − | − |
| pMON69827 | BN_G1540 | − | − | − | − | − | − | − | − | − | − |
| Control | SP30052 | − | − | − | − | − | − | − | − | − | − |

TABLE 2

P-BN.SW2-0:1:2 Expression in Developing Canola Siliques

| | | Days After Pollination | | | | | | | | |
|---|---|---|---|---|---|---|---|---|---|---|
| Construct | Event | 3 | 6 | 9 | 12 | 15 | 20 | 25 | 30 | 35 | 40 |
| pMON69825 | BN_G1474 | − | − | − | − | − | − | − | − | − | − |
| pMON69825 | BN_G1475 | − | − | − | − | − | − | − | − | − | − |
| pMON69825 | BN_G1476 | + | + | + | + | NA | + | + | + | + | + |
| pMON69825 | BN_G1477 | − | + | + | + | NA | + | + | − | − | − |
| pMON69825 | BN_G1478 | − | − | − | − | − | − | − | − | − | − |
| pMON69825 | BN_G1479 | − | ND | + | + | − | − | − | − | − | − |
| pMON69825 | BN_G1536 | − | − | − | − | − | − | − | − | − | + |
| pMON69825 | BN_G1537 | − | − | − | − | + | + | + | − | − | − |
| pMON69825 | BN_G1538 | + | − | − | − | + | + | − | − | − | − |
| pMON69825 | BN_G1580 | − | − | − | − | − | − | − | − | − | − |
| Control | SP30052 | − | − | − | − | − | − | − | − | − | − |

TABLE 3

P-BN.SW3-0:1:2 Expression in Developing canola Siliques

| | | Days After Pollination | | | | | | | | |
|---|---|---|---|---|---|---|---|---|---|---|
| Construct | Event | 3 | 6 | 9 | 12 | 15 | 20 | 25 | 30 | 35 | 40 |
| pMON69831 | BN_G1839 | + | + | + | + | + | − | + | + | + | + |
| pMON69831 | BN_G1901 | − | − | − | − | − | − | − | − | − | − |
| pMON69831 | BN_G1902 | − | − | − | − | − | − | − | − | − | − |
| pMON69831 | BN_G1903 | − | − | − | − | − | − | − | − | − | − |
| pMON69831 | BN_G1904 | − | − | − | − | − | − | − | − | − | − |
| pMON69831 | BN_G1905 | − | − | − | + | + | + | − | − | − | − |
| pMON69831 | BN_G1906 | − | − | + | + | + | + | + | + | + | + |
| pMON69831 | BN_G1907 | − | − | − | − | + | + | + | − | − | − |
| pMON69831 | BN_G1908 | − | − | − | − | + | − | + | − | − | − |
| pMON69831 | BN_G1951 | − | − | − | − | − | − | − | − | − | − |
| Control | SP30052 | − | − | − | − | − | − | − | − | − | − |

The data in Tables 1-3 indicate that the three promoters, P-BN.SW1-0:1:2 (SEQ ID NO: 7), P-BN.SW2-0:1:2 (SEQ ID NO: 8), and P-BN.SW3-0:1:2 (SEQ ID NO: 9) are capable of driving silique wall expression in *Arabidopsis* and Canola.

EXAMPLE 6

This example describes the construction of plant transformation vectors containing the P-BN.SW3-0:1:2 promoter operably linked to the *Arabidopsis thaliana* isocitrate lyase gene. To facilitate cloning, the P-BN.SW3-0:1:2 promoter was amplified using pMON69830 as a template with the following primers:

19944
[SEQ ID NO: 20]
5'-CCCGGGCTGGTCCTGCGAAGATTCTCAG-3',
and

19945
[SEQ ID NO: 21]
5'-CTCGAGCGGCCGCTTCTATGTCGACTGGAAAGAAAAAGTTGTGCCA
ACAAAAG-3'.

The reactions were run under conditions recommended by the Expand High Fidelity enzyme manufacturer (Roche Applied Biosciences, Indianapolis, Ind.). The product of the PCR reaction was purified according to standard methodology well known in the art and cloned into pCR2.1 Topo (Invitrogen) according to the manufacturer's instructions. The resulting plasmid was named pMON79578.

A 910-base pair fragment containing P-Bn.SW3-0:1:2 [SEQ ID NO: 9] was removed from the vector pMON79578 by digestion with SmaI and NotI. The fragment was cloned into pMON82374 which had been digested with PmeI and NotI in place of the pBr.Snap2 promoter. The vector pMON82374 contains a nopaline T-DNA right border sequence and octopine T-DNA left border sequence, with 2 expression cassettes contained between the 2 T-DNA borders. The first cassette contains the pBr.Snap2 promoter and T-Br-.Snap2-1 terminator. The second cassette contains with a 35S promoter from the Figwort Mosaic Virus (FMV) between the 2 T-DNA borders, driving the expression of a chimeric EPSP synthase gene containing a chloroplast targeting sequence from the *Arabidopsis* EPSP synthase gene (GenBank identifier number gi:16272) linked to a synthetic EPSP synthase coding region (U.S. Pat. No. 5,633,435) and the 3' untranslated region from the pea rbcS E9 gene. Additionally, pMON82374 contains recognition sites for cre recombinase. The recombinase sites are 5' of the FMV promoter and 3' of the E9 3' UTR. The resulting plasmid was named pMON79581.

A 2111 fragment containing L-At.ICL, CR-At.ICL, and T-At.ICL was removed from EST clone pMON82360 by digestion with SalI and NotI restriction enzymes and cloned between the pBr.Snap2 promoter and T-Br.Snap2-1 3' UTR in the SalI and Not I digested pMON79581. The resulting plasmid was named pMON79583. The nucleic acid sequence was determined using known methodology and confirmed the integrity of the cloning junctions. pMON79583 was used for the transformation of *Brassica napus*.

An 891-base pair fragment [SEQ ID NO: 22] containing the P-Bn.SW3-0:1:2 promoter sequence [SEQ ID NO: 9], was removed from the vector pMON79578 by digestion with SmaI and SalI. The fragment was cloned into DMRUEZ03.0112 which had been digested with PacI and SalI. Prior to SalI digestion and gel purification, the PacI overhang was blunt ended using Pfu polymerase according to the manufacturer's instructions (Stratagene). The resulting plasmid contains the nopaline T-DNA right border sequence and octopine T-DNA left border sequence, between which are the promoter, 5' UTR and first intron from the *Arabidopsis* act7 gene driving the expression of a CP4 EPSP synthase gene. This CP4 EPSP synthase gene comprises a CTP, linked to a synthetic EPSP synthase coding region and the 3' UTR from the pea rbsc E9 gene; the P-Bn.SW3-0:1:2 promoter operably linked to the *Arabidopsis thaliana* isocitrate lyase gene (as described in PCT Application WO 03/79766) and the napin 3' UTR. The nucleic acid sequence was determined using known methodology and confirmed the integrity of the cloning junctions. The resulting plasmid was named pMON82378 was used for the transformation of soybean.

EXAMPLE 7

This example sets forth the transformation of soybean plants with the constructs described in Example 5.

Soybean plants were transformed using an *Agrobacterium*-mediated transformation method, as described by Martinell (U.S. Pat. No. 6,384,301). For this method, overnight cultures of *Agrobacterium tumefaciens* containing the plasmid that includes a gene of interest, such as pMON75201, were grown to log phase and then diluted to a final optical density of 0.3 to 0.6 using standard methods known to one skilled in the art. These cultures were used to inoculate the soybean embryo explants prepared as described below. Briefly, the method is a direct germline transformation into individual soybean cells in the meristem of an excised soybean embryo. The soybean embryo is removed after surface sterilization and germination of the seed. The explants are then plated on OR media, a standard MS medium as modified by Barwale et al. (1986), plus 3 mg/L BAP, 200 mg/L carbenicillin, 62.5 mg/L cefotaxime, and 60 mg/L benomyl, and stored at 15° C. overnight in the dark. The following day the explants are wounded with a scalpel blade and inoculated with the *Agrobacterium* culture prepared as described above. The inoculated explants are then cultured for 3 days at room temperature. Following the post-transformation culture, the meristematic region is then cultured on standard plant tissue culture media in the presence of the herbicide glyphosate (Monsanto Company, St. Louis, Mo.), which acts as both a selection agent and a shoot inducing hormone. Media compositions and culture lengths are detailed in the aforementioned Martinell patent. After 5 to 6 weeks, the surviving explants that have a positive phenotype are transferred to soil and grown under greenhouse conditions until maturity.

The mature seeds of the transformed plants are harvested and analyzed for oil content using standard methodology, for example by near-infrared reflectance (NIR) spectroscopy as described in Williams and Norris (1987). The seeds from plants expressing the *Arabidopsis thaliana* isocitrate lyase gene, driven by the P-Bn.SW3-0:1:2 promoter, have a higher oil content as compared to seeds from non-transformed plants.

REFERENCES

The references listed below are incorporated herein by reference to the extent that they supplement, explain, provide a background for, or teach methodology, techniques, and/or compositions employed herein.
U.S. Patent No. Appln. 2002/0192812
U.S. Patent No. Appln. 2003/0028917
U.S. Pat. No. 4,810,648

U.S. Pat. No. 4,965,188
U.S. Pat. No. 4,990,607
U.S. Pat. No. 5,015,580
U.S. Pat. No. 5,094,945
U.S. Pat. No. 5,097,025
U.S. Pat. No. 5,110,732
U.S. Pat. No. 5,164,316
U.S. Pat. No. 5,176,995
U.S. Pat. No. 5,196,525
U.S. Pat. No. 5,229,114
U.S. Pat. No. 5,304,730
U.S. Pat. No. 5,322,938
U.S. Pat. No. 5,352,605
U.S. Pat. No. 5,359,142
U.S. Pat. No. 5,362,865
U.S. Pat. No. 5,378,619
U.S. Pat. No. 5,384,253
U.S. Pat. No. 5,391,725
U.S. Pat. No. 5,424,200
U.S. Pat. No. 5,428,147
U.S. Pat. No. 5,447,858
U.S. Pat. No. 5,463,175
U.S. Pat. No. 5,491,084
U.S. Pat. No. 5,512,466
U.S. Pat. No. 5,516,671
U.S. Pat. No. 5,516,671
U.S. Pat. No. 5,538,880
U.S. Pat. No. 5,543,576
U.S. Pat. No. 5,550,318
U.S. Pat. No. 5,589,583
U.S. Pat. No. 5,591,616
U.S. Pat. No. 5,599,670
U.S. Pat. No. 5,608,144
U.S. Pat. No. 5,608,149
U.S. Pat. No. 5,614,399
U.S. Pat. No. 5,627,061
U.S. Pat. No. 5,633,435
U.S. Pat. No. 5,633,441
U.S. Pat. No. 5,635,055
U.S. Pat. No. 5,659,122
U.S. Pat. No. 5,689,041
U.S. Pat. No. 5,716,837
U.S. Pat. No. 5,720,871
U.S. Pat. No. 5,750,876
U.S. Pat. No. 5,773,696
U.S. Pat. No. 5,824,877
U.S. Pat. No. 5,898,096
U.S. Pat. No. 5,942,664
U.S. Pat. No. 5,958,745
U.S. Pat. No. 5,981,840
U.S. Pat. No. 5,985,605
U.S. Pat. No. 5,998,700
U.S. Pat. No. 6,011,199
U.S. Pat. No. 6,013,864
U.S. Pat. No. 6,040,497
U.S. Pat. No. 6,063,597
U.S. Pat. No. 6,063,756
U.S. Pat. No. 6,072,103
U.S. Pat. No. 6,080,560
U.S. Pat. No. 6,093,695
U.S. Pat. No. 6,096,950
U.S. Pat. No. 6,110,464
U.S. Pat. No. 6,121,436
U.S. Pat. No. 6,160,208
U.S. Pat. No. 6,166,292
U.S. Pat. No. 6,171,640
U.S. Pat. No. 6,228,992
U.S. Pat. No. 6,232,526
U.S. Pat. No. 6,316,407
U.S. Pat. No. 6,380,466
U.S. Pat. No. 6,384,301
U.S. Pat. No. 6,384,301
U.S. Pat. No. 6,399,861
U.S. Pat. No. 6,403,865
U.S. Pat. No. 6,444,876
U.S. Pat. No. 6,448,387
U.S. Pat. No. 6,476,295
U.S. Pat. No. 6,476,295
U.S. Pat. No. 6,476,295
U.S. Pat. No. 6,506,565
U.S. Pat. No. 6,506,962
U.S. Pat. No. 6,531,648
U.S. Pat. No. 6,537,750
Barwale et al., *Plants,* 167:473-481, 1986.
Bechtold et al., *C.R. Acad. Sci. Life Sciences,* 316:1194-1199, 1993.
Bent et al., *Science,* 265:1856-1860, 1994.
DeBlock et al., *EMBO J.,* 6:2513-2519, 1987.
Misawa et al, *Plant J.,* 4:833-840, 1993.
Misawa et al, Plant J., 6:481-489, 1994.
Murashige and Skoog, *Physiol. Plant,* 15:473-497, 1962.
Orman et al., *JAOCS,* 69(10):1036-1038, 1992.
Patrick et al., *JAOCS,* 74(3):273-276, 1997.
PCT Appln. WO 03/79766
Rubel, *JAOCS,* 71:1057-1062, 1994.
Sambrook et al., In: *Molecular cloning*, Cold Spring Harbor Laboratory Press, Cold Spring Harbor, N.Y., 2000.
Sathasiivan et al., *Nucl. Acids Res.,* 18:2188-2193, 1990.
Tiwari et al., *JAOCS,* 51:104-109, 1974.
Williams and Norris, In: *Near-infrared Technology in the Agricultural and Food Industries*, Amer. Assoc. Cereal Chemists, Inc., St. Paul, Minn., 1987.

What is claimed is:

1. A construct comprising a promoter operably linked to a heterologous transcribable polynucleotide molecule, wherein the promoter comprises the polynucleotide sequence of SEQ ID NO:7.

2. The construct of claim 1, wherein the transcribable polynucleotide molecule is operably linked to a 3' transcription termination polynucleotide molecule.

3. The construct of claim 1, wherein said transcribable polynucleotide molecule is a gene of agronomic interest.

4. The construct of claim 1, wherein said transcribable polynucleotide molecule is a marker gene.

5. A transgenic plant stably transformed with the construct of claim 1.

6. The transgenic plant of claim 5, wherein the transgenic plant is a dicotyledonous plant.

7. The transgenic plant of claim 6, wherein the dicotyledonous plant is selected from the group consisting of tobacco, tomato, potato, soybean, cotton, canola, sunflower, and alfalfa.

8. The transgenic plant of claim 5, wherein the transcribable polynucleotide molecule confers altered cell proliferation in the seed of said transgenic plant.

9. The transgenic plant of claim 5, wherein the transcribable polynucleotide molecule confers altered oil content in the seed of said transgenic plant.

10. The transgenic plant of claim 5, wherein the transcribable polynucleotide molecule confers altered protein quality in the seed of said transgenic plant.

11. The transgenic plant of claim 5, wherein said transcribable polynucleotide molecule confers altered micronutrient content to said transgenic plant.

12. A seed of the transgenic plant of claim 5, wherein the seed comprises said construct.

13. Oil of the transgenic plant of claim 5, wherein the oil comprises a detectable nucleic acid comprising the construct of claim 1.

14. Meal of the transgenic plant of claim 5, wherein the meal comprises a detectable nucleic acid comprising the construct of claim 1.

15. A transformed plant cell having stably incorporated into its genome the construct of claim 1.

16. A method of making a vegetable oil, comprising the steps of:
    a) obtaining the seed of claim 12; and
    b) extracting oil from the seed.

17. A method of making a vegetable protein, comprising the steps of:
    a) obtaining the seed of claim 12; and
    c) extracting the protein from the seed.

18. A method of directing expression of a transcribable polynucleotide sequence in a plant cell comprising transforming a plant cell with a promoter operably linked to the transcribable polynucleotide sequence, wherein the promoter comprises the polynucleotide sequence of SEQ ID NO:7.

19. The method of claim 18, comprising regenerating a plant from the plant cell.

20. A method of preparing food or feed comprising:
    a) obtaining the transgenic plant of claim 5; and
    b) preparing food or feed from said plant or a part thereof.

* * * * *

SEQUENCE LISTING

<160> NUMBER OF SEQ ID NOS: 22

<210> SEQ ID NO 1
<211> LENGTH: 1653
<212> TYPE: DNA
<213> ORGANISM: Brassica napus

<400> SEQUENCE: 1

```
ctgttatatg ttattactta tgaggaactg gtattacata tagagaaaaa tatagatcga      60
gaacaccaaa ttatcataaa tatggaactc tgtggttatt aaaaagtttt gttatacgat     120
```

-continued

```
tttatgttct tttaaaagtg tttaatgggg ttgattgtat gatcacaata tatgttatac    180
atgatcgtgc gttcacccac tctgatatga ttgttcatgg ggagttttgt atagaattaa    240
gtgaaattat tagaatttac aataagatca ctaagcagat attttcataa tatttttta    300 taaaccctat cggctgatcc gatcggctcc gggaggaacg cgcttagtga aatattttca    360 taatatttt catgacatca actgtgagtg tcacttagaa tctcgaatat aatccaaatc    420
cgacataaga tatgattctc ttattcttgc attcaaccga ataatctgaa gtgctccaat    480
cgcaaactcg ttttctcgcc catgacctaa aaatggtctt ttatataatg cgcatatgat    540
taatccgcca ccaaagtgct tgtgaccac ttatttactt atttatatgc tgataactct    600
gtgttatgtg taaagttact aattagttta atatttataa gcaagagtaa gattctcatg    660
ataaacattt aaattagtat ctccagtatg attgtattca ataagtatta gctgaattaa    720
gctagttgat agtatatcat aattttgaca aatttaacgt aacaattttc ataatcattt    780
actgctgtta gaaacctgtg ttataattat aactttcctt tttgggtcaa aattacaact    840
ttctatacat aaaagagata acttaaagga aaggcagttg acttgagaat ataaagtcaa    900
ttggagagca atttgcagga gaaaagtcat aaaagtcgta cattcgccac ttgtaattaa    960
caagagaatc atcggaaaat ggcatctttg aaaataatat tggtaattta cgtaatacat   1020
tattggttaa taattttta aaaaatatat aatttatatt ggttttaag ccatatattg    1080 tctttggtta ttaagccact acggttaaga tatgccaagt tactttatta agatgcatat   1140
atactcactt ctattacata tatatggtaa tatatatgtt tctaaaacat agtattatat   1200
atgcaaacaa agtagaatat tagtcaattt taaaactagt tgcaatttaa aaaaaaaaa   1260 ttagacaact ttttacaaat gaaaccaatg ggacaggtgt aggaatagtg tcttcaatat   1320
gtgtatagat tagaaaatct tttgaggata tagtcatttg agtgtagcaa acataaccat   1380
gacatatgca tatgatgacc cacaagtgca tactggcagc atatacccgt ttgagcacct   1440
acatataact ttgaactaat aaatatttaa atgtatatga aaaaccttcg aatgatgaat   1500
gattaaattt taaaccaaac tatgatctgg cattggctaa tagcttcaca cttcgttggc   1560
acgtctattt aaagcttcac aaagacgcga acttaaatca caacccgaaa acgaaaaata   1620
tcacaagaaa agaaaaaaaa accatttatt cac                              1653
```

<210> SEQ ID NO 2
<211> LENGTH: 27
<212> TYPE: DNA
<213> ORGANISM: Artificial
<220> FEATURE:
<223> OTHER INFORMATION: primer sequence

<400> SEQUENCE: 2
caccatgctt tcacgtcttt tgagttg                                       27

<210> SEQ ID NO 3
<211> LENGTH: 22
<212> TYPE: DNA
<213> ORGANISM: artificial
<220> FEATURE:
<223> OTHER INFORMATION: primer sequence

<400> SEQUENCE: 3
gtaatacgac tcactatagg gc                                            22

<210> SEQ ID NO 4
<211> LENGTH: 30

```
<212> TYPE: DNA
<213> ORGANISM: artificial
<220> FEATURE:
<223> OTHER INFORMATION: primer sequence

<400> SEQUENCE: 4
cccacagatt ttctatttcg gttctcatac                                         30

<210> SEQ ID NO 5
<211> LENGTH: 19
<212> TYPE: DNA
<213> ORGANISM: Artificial
<220> FEATURE:
<223> OTHER INFORMATION: primer sequence

<400> SEQUENCE: 5
actatagggc acgcgtggt                                                     19

<210> SEQ ID NO 6
<211> LENGTH: 23
<212> TYPE: DNA
<213> ORGANISM: Artificial
<220> FEATURE:
<223> OTHER INFORMATION: primer sequence

<400> SEQUENCE: 6
gagaaaccat ggtgaataaa tgg                                                23

<210> SEQ ID NO 7
<211> LENGTH: 1288
<212> TYPE: DNA
<213> ORGANISM: Brassica napus

<400> SEQUENCE: 7
gggctggtga ttatgattcg atgatttgat ccagttagtt aattttgtcg aatcattttc        60
ttctttcttc gtttaaacat ttaacttgca cgaatggttc tcttgtgatt gaacggaatc       120
tttgaatcaa attaattaat tgataagaag acaaataaag attccatgtt ttgataagat       180
taatgatttt gatgcattaa cggcatattt gaaacaaatt cattaatcag caaaactgag       240
aattttgaac tacgaaattc cagtttctag ttgaaaaaat aatgatcgta gagaacatat       300
tataaaacct cagaaacgaa ctatgtagta gaaattggtt aactgtattt agcaaacaaa       360
aaagcgttaa ctgttaccat aacccattat tttaattcct aaattatgca aattgcaagc       420
ttccaatctt agcctttaa ataaaaaaga cgctatggac ttcgaatcag attgtgaaca        480
acttgtggaa ctaattaaca gagaagaaac tgaccagcga tggcagtgga gctagatgag       540
attaaagcct atgcaacaag atttatggag ttttcgatat tgtttatcct tagagctcta       600
aacgtccgtg cagatggaga tgctcctcgg aggatggctc gtctgttccc acttgatcta       660
gcctagatgg atagacaaca gaaaaaaaaa aaaaatgtcc gtgcacatgg caggcgctag       720
atcatgagtc ctcaggttcc cctctgtaaa cggttgttca cccgatggct agtacctaat       780
actggtcata actcatacgg atgcagacca gtaagctgga ttgattttt tcgatgtcaa        840 aaaaaaaga cgctatgatc ctaataaaaa cagggtaaac atacataaat gatataagtt        900
tagtagctca aaattgctag tttccaacaa atgttttct gatcctattt tcaggttttt        960
gtaacaaata taatttttaa atgtttccct taatatttgt ttttcaattt tatatcaata      1020
aatatatttg tccaaatacc aatcagtatc caagttcggt atcgttaagc cttgggagat      1080
taaagtctaa taggttcgaa ccatgatgag ttctagttat ctacatagat gtataagatg      1140
atcattactt gtaaactaaa aatactttgt cataatcact tcatagaaca ttaccagtag      1200
```

```
tatcacactt ttttcactat aaaaccccac tgcgaaaccc ttttggagta atcaaactag    1260
tatctaaatc cttcaacttt tctaagac                                      1288
```

<210> SEQ ID NO 8
<211> LENGTH: 848
<212> TYPE: DNA
<213> ORGANISM: Brassica napus

<400> SEQUENCE: 8

```
gggctggtct gaaggacaag gatgatcgga tatctgcgtt ggaggctcag atggcagctc     60
aacaggcggg ctatgagacc cagaagaggc tgaacgagca gatgatggac atgatgaaga    120
ggatgtaccg aacgagacgt tcccgaacat tcaagacccg tagttttttt ttttccaaaa    180
actctgaatg ttttatttaa atttgaatat tatctactat gttttatttt atgttttatt    240
carttttaat tttaatttta aaaattttaa tttttttcca aaaaaaaata atttttaaaa    300
aaaataaatt ttttaaaaaa ataatttttt tcaaaattcc gagggaatgg aggtcctcgg    360
ataattccga ggaacttta tcctcggtaa attccgacga rcattaagtt cctcggaatt     420
gtctgaggga aaggattcct cggaattttc cgagaaactc aattccctcg gaaaattccg    480
agraatattt cgtcgaaact tccgaggatg gaccatcgga attccttcgg tattttccga    540
ggaaccttcc gacgaacatt gtgccctcgg agtttcctcg gaattttgtt tcctcggaat    600
tccgtcggaa aattccgacg gaattccgag gaatttgaat ttccgaggag ttatttccga    660
ggactttttt cgtcggtatg tcctcggaat aacgttattc cgacgacata ccgacgattt    720
tttccctcag tatcccgatg ttttcttgta gtgtttatgc attatataaa cccatcgatt    780
caatcagtct catcatccaa ttaccttaa acttaaactt ctggtttctc aaaaaatatt    840
ggccttac                                                            848
```

<210> SEQ ID NO 9
<211> LENGTH: 874
<212> TYPE: DNA
<213> ORGANISM: Brassica napus

<400> SEQUENCE: 9

```
cctgcgaaga ttctcagcac caagacccat ctcttttagg gttatttgag atgcccgtat     60
aaaagaggaa aaggtgggtg acttgaagag gacggcaaca acatcagatt gtggagagca    120
ggtgaaattg attgtcttgg ttaaaagatc gtcgtagcat acctgagcat acatcaatca    180
agttataaga actagatata tagttcatag ctctattatt cggtgtagaa gtgattagag    240
ctttacttct cttgattact cttttgtactt gagatagtgg attgaaagcg tagttcttcc    300
ccagacgtac cgcaaaggga actgggtaac caaagctttg tgtcttgtct cctatacaac    360
aaacaaacaa attgtatcaa gttaattgat caagcattag ctaaacaaat ctagctaagg    420
aactaaggtt taagacagta atacaatcta agaccttaca atatattgga gaatttattc    480 tggttttta ataatcatgc aaatttaagt cgttactaat tacgtaccaa caccaaatta    540
tcccattata ctgtagcaaa aatgatgtgt aagtgtatat aaatacttgt gtaatcccat    600
ccttaatgat taattaatta ttacaatatc gaatccttga cttcactcaa acacgttcac    660
gatggcgtca tctgatgcaa cacaagatat taatacttac acgtatatat acacacacat    720
aagtacatat atatacgtgt aaaacatgag attctatttg cgagtctttg tctatataag    780
ttccaacttt tctcacagtt gtgtcttctt ttcctacctc gccgctcttc aaccaaaata    840
atccctaact tttgttggca caactttttc tttc                                874
```

<210> SEQ ID NO 10
<211> LENGTH: 29
<212> TYPE: DNA
<213> ORGANISM: Artificial
<220> FEATURE:
<223> OTHER INFORMATION: primer sequence

<400> SEQUENCE: 10
ttcatatctg cgtaagtacg tccatgttc                              29

<210> SEQ ID NO 11
<211> LENGTH: 30
<212> TYPE: DNA
<213> ORGANISM: Artificial
<220> FEATURE:
<223> OTHER INFORMATION: primer sequence

<400> SEQUENCE: 11
cgagaaacag aatgatgaaa ctagagagac                             30

<210> SEQ ID NO 12
<211> LENGTH: 27
<212> TYPE: DNA
<213> ORGANISM: Artificial
<220> FEATURE:
<223> OTHER INFORMATION: primer sequence

<400> SEQUENCE: 12
caccatgctt tcacgtcttt tgagttg                                27

<210> SEQ ID NO 13
<211> LENGTH: 26
<212> TYPE: DNA
<213> ORGANISM: Artificial
<220> FEATURE:
<223> OTHER INFORMATION: primer sequence

<400> SEQUENCE: 13
tcgatgccac gaaaatgcat aagaac                                 26

<210> SEQ ID NO 14
<211> LENGTH: 26
<212> TYPE: DNA
<213> ORGANISM: Artificial
<220> FEATURE:
<223> OTHER INFORMATION: primer sequence

<400> SEQUENCE: 14
cctcatcctc atcctcatcc tcaacc                                 26

<210> SEQ ID NO 15
<211> LENGTH: 29
<212> TYPE: DNA
<213> ORGANISM: Artificial
<220> FEATURE:
<223> OTHER INFORMATION: primer sequence

<400> SEQUENCE: 15
ccgtacacgg taaaatagtt cttgacgga                              29

<210> SEQ ID NO 16
<211> LENGTH: 26
<212> TYPE: DNA
<213> ORGANISM: Artificial
<220> FEATURE:
<223> OTHER INFORMATION: primer sequence

```
<400> SEQUENCE: 16
ctaaagccat ggtcttagaa aagttg                                          26

<210> SEQ ID NO 17
<211> LENGTH: 24
<212> TYPE: DNA
<213> ORGANISM: Artificial
<220> FEATURE:
<223> OTHER INFORMATION: primer sequence

<400> SEQUENCE: 17
aatacgactc actatagggc acgc                                            24

<210> SEQ ID NO 18
<211> LENGTH: 25
<212> TYPE: DNA
<213> ORGANISM: Artificial
<220> FEATURE:
<223> OTHER INFORMATION: primer sequence

<400> SEQUENCE: 18
gaaaagccat ggtaaggcca atatt                                           25

<210> SEQ ID NO 19
<211> LENGTH: 25
<212> TYPE: DNA
<213> ORGANISM: Artificial
<220> FEATURE:
<223> OTHER INFORMATION: primer sequence

<400> SEQUENCE: 19
cttctgccat ggaaagaaaa agttg                                           25

<210> SEQ ID NO 20
<211> LENGTH: 28
<212> TYPE: DNA
<213> ORGANISM: Artificial
<220> FEATURE:
<223> OTHER INFORMATION: primer sequence

<400> SEQUENCE: 20
cccgggctgg tcctgcgaag attctcag                                        28

<210> SEQ ID NO 21
<211> LENGTH: 53
<212> TYPE: DNA
<213> ORGANISM: Artificial
<220> FEATURE:
<223> OTHER INFORMATION: primer sequence

<400> SEQUENCE: 21
ctcgagcggc cgcttctatg tcgactggaa agaaaaagtt gtgccaacaa aag            53

<210> SEQ ID NO 22
<211> LENGTH: 891
<212> TYPE: DNA
<213> ORGANISM: Brassica napus

<400> SEQUENCE: 22
gggctggtcc tgcgaagatt ctcagcacca gacccatct cttttagggt tatttgagat      60
gcccgtataa aagaggaaaa ggtgggtgac ttgaagagga cggcaacaac atcagattgt    120
ggagagcagg tgaaagttga ttgtcttggt taaaagatcg tcgtagcata cctgagcata    180
catcaatcaa gttataagaa ctagatatat agttcatagc tctattattc ggtgtagaag    240
```

```
tgattagagc tttacttctc ttgtattact ctttgtactt gagatagtgg attgaaagcg    300
tagttcttcc ccagacgtac cgcaaaggga actgggtaac caaagctttg tgtcttgtct    360
cctatacaac aaacaaacaa attgtatcaa ggttaattga tcaagcatta gctaaacaaa    420
tctagctaag gaactaaggt ttaagacagt aatacaatct aagaccttac aatatattgg    480
agaatttatt ctggttttt aataatcatg caaatttaaa gtcgttacta attacgtacc     540
aacaccaaat tatcccatta tactgtagca aaaatgatgt gtaagtgtat ataaatactt    600
gtgtaatccc atccttaatg attaattaat tattacaata tcgaatccct tgacttcact    660
caaacacgtt cacgatggcg tcatctgatg caacacaaga tattaatact tacacgtata    720
tatacacaca cataagtaca tatatatacg tgtaaaacat gagattctat ttgcgaagtc    780
tttgtctata taagttccaa cttttctcac agttgtgtct tcttttccta cctcgccgct    840
cttcaaccaa aataatccct aactttttgtt ggcacaactt tttctttcca g            891
```